United States Patent [19]

Rotman

[11] Patent Number: 4,749,575
[45] Date of Patent: Jun. 7, 1988

[54] MICROENCAPSULATED MEDICAMENT IN SWEET MATRIX

[75] Inventor: Avner Rotman, Rehovot, Israel
[73] Assignee: Bio-Dar Ltd., Rehovot, Israel
[21] Appl. No.: 823,798
[22] Filed: Jan. 29, 1986

Related U.S. Application Data

[63] Continuation-in-part of Ser. No. 538,801, Oct. 3, 1983, abandoned.

[51] Int. Cl.$^4$ ............................ A61K 9/22; A61K 9/52
[52] U.S. Cl. ................................. 424/441; 424/440; 424/457; 424/468; 424/490
[58] Field of Search ............... 426/616, 613, 631, 660, 426/572, 72, 74; 424/22, 48, 17, 440, 490, 457, 468, 441; 514/777

[56] References Cited

U.S. PATENT DOCUMENTS

| | | | |
|---|---|---|---|
| 2,538,202 | 1/1951 | Kimball | 426/74 |
| 2,634,210 | 4/1953 | Kimball | 426/72 |
| 2,957,804 | 10/1960 | Shuyler | 424/17 |
| 3,520,970 | 7/1970 | Lehmann et al. | 424/25 |
| 3,697,641 | 10/1972 | Ahrens | 426/72 |
| 3,775,537 | 11/1973 | Lehmann et al. | 424/21 |
| 3,814,819 | 6/1974 | Morgan | 426/72 |
| 3,821,422 | 6/1974 | Morse et al. | 426/72 |
| 3,835,221 | 9/1974 | Fulberth et al. | 424/20 |
| 3,860,733 | 1/1975 | Morse et al. | 426/302 |
| 3,954,959 | 5/1976 | Pedersen | 424/21 |
| 3,962,416 | 6/1976 | Katzen | 426/74 |
| 3,992,555 | 11/1976 | Kovacs | 426/72 |
| 3,992,556 | 11/1976 | Kovacs | 426/72 |
| 4,000,322 | 12/1976 | Billerbeck et al. | 426/72 |
| 4,018,900 | 4/1977 | Hayward et al. | 426/72 |
| 4,018,901 | 4/1977 | Hayward et al. | 426/72 |
| 4,038,423 | 7/1977 | Hayward et al. | 426/72 |
| 4,049,832 | 9/1977 | Hayward et al. | 426/72 |
| 4,062,986 | 12/1977 | Billerbeck et al. | 426/72 |
| 4,083,949 | 4/1978 | Benedikt | 424/19 |
| 4,101,651 | 7/1978 | Kobayashi et al. | 424/35 |
| 4,102,806 | 7/1978 | Kondo et al. | 426/72 |
| 4,152,462 | 5/1979 | Hayward et al. | 426/72 |
| 4,153,735 | 5/1979 | Mommer | 426/72 |
| 4,182,778 | 1/1980 | Hall et al. | 426/72 |
| 4,191,783 | 3/1980 | Burkwall | 426/72 |
| 4,230,687 | 10/1980 | Sair et al. | 426/72 |
| 4,271,142 | 6/1981 | Puglia et al. | 424/14 |
| 4,284,652 | 8/1981 | Christenson | 426/72 |
| 4,327,077 | 8/1982 | Puglia et al. | 424/38 |
| 4,490,352 | 12/1984 | Miller | 424/17 |
| 4,543,262 | 9/1985 | Michnowski | 426/72 |
| 4,587,118 | 5/1986 | Hsiao | 424/19 |

FOREIGN PATENT DOCUMENTS

| | | |
|---|---|---|
| 900749A | 2/1985 | Belgium . |
| 3435747A | 4/1985 | Fed. Rep. of Germany . |
| 717369 | 1/1932 | France .................... 424/17 |
| 68083 | 3/1958 | France .................... 424/17 |
| 2496403 | 6/1982 | France .................... 424/17 |
| 2552665 | 4/1985 | France . |
| 164102 | 12/1981 | Japan ..................... 424/17 |
| 46901 | 3/1982 | Japan ..................... 424/17 |
| 13503 | 1/1983 | Japan ..................... 424/17 |
| 60-94058 | 5/1985 | Japan . |
| 102138A | 6/1985 | Japan . |
| 8403003 | 5/1985 | Netherlands . |
| 519858 | 4/1972 | Switzerland . |
| 875763 | 8/1961 | United Kingdom . |
| 1297221 | 11/1972 | United Kingdom . |
| 1342974 | 1/1974 | United Kingdom . |
| 1439240 | 6/1976 | United Kingdom . |
| 2057847 | 4/1981 | United Kingdom . |
| 1598458 | 9/1981 | United Kingdom . |
| 2092425 | 8/1982 | United Kingdom . |
| 2147501A | 5/1985 | United Kingdom . |

OTHER PUBLICATIONS

Chemical Abstracts, 78-151637 (1973).
Derwent Abstract of Rotman-V, Belgium 900749-A (01-02-85), Australian Patent Abstract of Rotman-VI--AV-A-33799184 (18-4-85).
Lockman et al., "The Theory & Practice of Indust. Pharmy, 2nd Ed., Lea & Febiger, 1976, p. 420.
Chem Abstracts 98:70502N, "Stability of Food Fortified with Vit. A microcapsules, (1983), Li et al.

*Primary Examiner*—Shep K. Rose
*Attorney, Agent, or Firm*—Browdy and Neimark

[57] ABSTRACT

Any orally administrable medicament is prepared into a dosage form which eliminates the unpleasant taste and mouth feel of the medicament and is easily and pleasantly ingested even by children, by microencapsulating the medicament into microcapsules of less than 300 microns diameter, and embedding the microcapsules into a soft, sweet, palatable matrix, such as chocolate.

10 Claims, No Drawings

MICROENCAPSULATED MEDICAMENT IN SWEET MATRIX

CROSS-REFERENCE TO RELATED APPLICATION

The present invention is a continuation-in-part of application Ser. No. 538,801, filed Oct. 3, 1983, now abandoned the entire contents of which are hereby incorporated by reference.

FIELD OF THE INVENTION

The present invention relates to a manner in which medicaments may be orally administered to children or others in a pleasant manner in which the taste of the medicament is totally hidden. More particularly, the present invention relates to a medicament form for permitting such administration.

BACKGROUND OF THE INVENTION

Oral medication is one of the most popular methods of drug administration into the body because it enables self-medication of the patient. In this category, palatability is an extremely important factor in formulating pharmaceutical forms. Because of the strong unpleasant taste of many medicaments, the value of many drugs is substantially diminished. This is particularly common among children's medications, but is also true for adults. In order to overcome these problems of unpleasant taste and unpalatable taste, many flavorings have been employed with pharmaceuticals. Thus, it is very common to administer many children's drugs as a flavored syrup. Unfortunately, flavoring merely masks the unpleasant mouth taste but affects the palatability only slightly. A number of medications have an especially bitter taste, and even adults reluctantly take them. In many such cases even syrups cannot mask the bitter taste, thus constituting a difficult pharmaceutical problem.

Among the flavorings which have been used for the purpose of masking is chocolate. Examples of patents in which chocolate is used in conjunction with medicaments, are U.S. Pat. Nos. 4,271,142 and 4,327,077 to Puglia et al, U.S. patent No. 3,697,641 to Ahrens, U.S. Pat. No. 199,139 to Clark, British Pat. No. 543,309 to Evans and Australian Pat. No. 7310/32 to Jones et al. Children's vitamins encased in chocolate are also known and on the market, but in these products some of the vitamins are not sufficiently stable. Laxatives in chocolate are also well known. In all of these, however, the unpleasant taste is merely masked and the medicines still adversely affect the flavor of the chocolate and the palatability of the medicine is not substantially improved. Furthermore, stability problems caused by direct contact of the drug with the chocolate can arise.

In order to permit the release of orally administered drugs within selected portions of the alimentary canal, i.e., the stomach or intestine, pills in which the medicament are protected with a desired coating have been developed. A more advanced pharmaceutical form for this purpose is the microencapsulated drug where one tablet or large capsule contains a few hundred tiny (approximately 0.5–0.8 mm) capsules, called microcapsules, containing the drug. The type of coating encapsulating the drug is chosen according to the medication desired and the desired release characteristics. Substained release coatings permit gradual release of medicament over time. Such encapsulated medicament heretofore has not been administrable in chewable form as breakage of any substantial number of microcapsules in the mouth might create an overdose condition.

It has been known to fortify food, including candies, with encapsulated vitamins. This was done to fortify the food rather than provide an improved dosage mode of administration of the vitamin.

SUMMARY OF THE INVENTION

Accordingly, it is an object of the present invention to provide a new form of medication for oral administration.

It is another object of the present invention to provide a new form of medicament for oral administration in which the unpalatable taste and mouth feel of the medicament is totally eliminated.

It is a further object of the present invention to provide a new form of medicament which is very palatable to children, as well as adults.

It is still a further object of the present invention to provide a form of medicament which is chewed and swallowed by the patient without substantial release of the medicament into the mouth during the chewing process.

It is yet a further object of the present invention to provide a new form of medicament which may be chewed and swallowed as a solid but in which the medicament passes through the stomach without release until reaching the intestines.

It is still another object of the present invention to provide a chewable sustained release medicament.

It is another object of the present invention to provide a method for administering medicaments for children in a manner which will be platable to the child.

It is still another object of the present invention to provide a method of administering medicaments in a solid form which may be chewed and then swallowed without release of medicament in the mouth.

It is still a further object of the present invention to provide such a method in which the medicament is not released in the stomach but which passes through the stomach at substantially the speed of a liquid.

These and other objects are obtained in accordance with the present invention by microencapsulating the drug to be administered and embedding the microcapsules in a soft, sweet palatable matrix, such as chocolate. The combination of encapsulation of the drug and the use of the soft, sweet matrix, such as chocolate, achieves the goals of both preventing the unpleasant taste which the drugs may possess and overcoming the palatability problem that may arise when one tries to ingest the drug itself. The encapsulation will prevent the unpleasant taste which many drugs possess and the chocolate matrix will serve as a way to overcome the palatability problem. Furthermore, the encapsulation will prevent the medication from giving an off-flavor to the chocolate itself, which inevitably occurs when drugs are mixed directly with a chocolate matrix without first being microencapsulated. Encapsulation also prevents loss of stability of the medicament by eliminating direct contact of the medicament with the chocolate.

This combination will totally eliminate the unpleasant taste of the medicines and the patient will only taste the chocolate or other soft, sweet matrix. Obviously, this system is superior to any other existing method.

If the size of the microcapsules of the medicament is small enough, release of the medicament within the microcapsules during the chewing process can be substantially avoided and it is substantially impossible to detect the presence of the microcapsules in the chocolate (or other soft sweet matrix). This is a particular advantage when the medicament is to be administered for sustained release. Capsules designed for sustained release contain much more medication than those designed for immediate release. Thus, any premature breakage of such capsules is a serious problem as a large dosage designed for gradual release will be released immediately and this could cause a serious overdose. If the microcapsules are small enough, there is no substantial breakage in the mouth upon chewing and, therefore, sustained release medicament can be administered in chewable form for the first time in accordance with the present invention.

Furthermore, if the microcapsules are sufficiently small in size they pass through the stomach in the same manner as a liquid while larger microcapsules are retained in the stomach for longer periods of time in the same manner as solids. This is a distinct advantage, for example, when the encapsulation is an enteric coating which prevents release in the stomach and permits release only in the intestine. Much faster release is obtained using the mode of administration of the present invention with the preferred microcapsule size because the small microcapsules enter the intestine much faster than larger conventional size microcapsules.

Accordingly, a particularly important aspect of the present invention is the use of microcapsules of a size smaller than 300$\mu$, which size has the unexpected advantage of permitting administration of a unit dosage of medicament in a soft, sweet matrix, such as chocolate, without substantially affecting the taste or mouth feel of the chocolate, without permitting substantial breakage of the microcapsules during chewing operation and permitting the microcapsules to be carried through the stomach in the same manner as liquids.

DETAILED DESCRIPTION OF PREFERRED EMBODIMENTS

As the soft, sweet matrix in accordance with the present invention, there may be used any palatable foodstuff which can be masticated without substantial chewing and easily swallowed, preferably a confection which is sweet to the taste and will be readily accepted by the child or adult. While chocolate is the preferred matrix, it should be understood that other soft, sweet matrices such as fudge, marshmallows, peanut butter, carob, solid yogurt, or even cookies of appropriate consistency may be used as the matrix, alone or in combination with other matrices. The matrix should not be hard or chewy, such as a hard or gummy candy, because the heavy pressure which would be involved in chewing such a matrix might break the microcapsules and thus destroy the purpose of the present invention. A soft chocolate, such as sweet or milk chocolate, is ideal for this purpose a substantial chewing is not required for complete mastication and the chocolate and embedded microcapsules can be masticated and swallowed without breaking the microcapsules. Other particularly preferred matrices are those which have substantially the same consistency as chocolate, such as carob and solid yogurt. The tests conducted with chocolate and referred to herein certainly apply to other matrices having substantially the same consistency as the chocolate tested.

The microcapsules should be of small size in order to ensure easy and pleasant palatability. It has been discovered that very small microcapsules with a size smaller than about 300 microns, are particularly preferred. The best product according to the present invention would be one in which substantially no medicament is released from the microcapsules during chewing of the matrix and the presence of the microcapsules is not detectable when masticating the matrix. It, of course, follows that the smaller the microcapsules the more microcapsules must be included in the same amount of matrix to provide the same unit dose of medicament. Commercial microcapsules are all mostly over 800$\mu$ in size, although some commercial products have a minor percent of the microcapsules thereof between 600 and 800$\mu$ (see Example 14, below). It has been discovered that when microcapsules of the size of such commercial microcapsules are used, the product in accordance with the present invention is unsatisfactory as substantial medicament is released in the mouth while chewing and a very gritty mouth feel is imparted to the matrix. On the other hand, when the size of the microcapsules is less than 300$\mu$, there is negligible release of medicament in the mouth and there is no more than a trace of grittiness. Even with such small microcapsules, sufficient loading of a unit size of matrix to make a unit dose can be obtained without substantially affecting the taste or mouth feel of the matrix. Accordingly, the microcapsules should be of a size below about 300$\mu$, preferably about 40 to about 300$\mu$. Even better results are obtained when the maximum size is maintained below about 250$\mu$, and the best results are obtained below about 150$\mu$.

Another advantage of particularly small microcapsules is the fact that microcapsules below 300$\mu$, and particularly those below about 200$\mu$, pass through the stomach much faster than larger microcapsules, such as those above 600$\mu$. It has been discovered that even if a medicament is coated with a gastric-resistant coating, medicament in microcapsules below 300$\mu$ is released several hours before that in microcapsules above about 600$\mu$. It is believed that the small microcapsules form a suspension in the stomach and are transported to the intestine in a similar way to a liquid, namely as soon as it is swallowed. However, the larger microcapsules, above about 600$\mu$, behave like solids which stay in the stomach for about 2-3 hours before leaving to the intestines. This is another unexpected and substantial advantage of the use of microcapsules below about 300$\mu$, rather than the heretofore commercially used size of over 600$\mu$.

A very wide range of medicaments are suitable for inclusion in the microcapsules used in the present invention. Such medicaments include antibiotics and other antibacterial agents, analgesics, antihistamines, decongestants, anti-inflammatory agents, anti-hypertensive agents, hypnotics, sedatives, tranquilizers, alkaloids, diuretics, vasodilators, hormones, vitamins or any other medicament frequently used in oral dosage form. Those with especially bitter taste, such as penicillin, are, of course, particularly suited for use in the present invention.

Suitable antibiotics include penicillins, cephalosporins, tetracyclines, chloramphenicol, streptomycins, and macrolids. Suitable fully synthetic anti-bacterial agents include nitrofurantoin and the sulphonimides. Suitable anti-inflammatory or analgesic agents include aspirin and acetaminophen. Suitable psychotropic medicaments include $\alpha$-methyldopa and guanethidine. Suitable diuretics include aminophyline and acetazolamide.

Antibacterials include benzylpenicillin, phenoxymethylpencillin, ampicillin and its pivaloyloxymethyl or phthalyl esters, amoxycillin, cloxicillin, dicloxicillin, flucloxicillin, carbenicillin, propicillin, methicillin, cephalexin, cephaloridine, cephaloglycine, cephalothin, tetracycline, oxytetracycline, chlorotetracycline, novobiocin, neomycin, chloramphenicol, sulphathiazole, succinyl sulphathiazole, sulphadimidine, streptamycin, erythromycin, fusidic acid, griseofulvin, kanamycin, lincomycin, spiromycin, sulphamethoxy pyrideazine, sulphaphenozole, salicylazosulphapyridine, sulphamethoxazole and trimethoprin.

Suitable vitamins or nutritional supplements include thiamine, nicotinamide, ascorbic acid, pyridoxine, riboflavine, tryptophane, pantothenates, glycerophosphates and mixtures of these and other vitamins.

Other medicaments include alcofenac, theophylline, hexobendine, xylamide, and 0-(4-methoxyphenylcarbomoyl)-3-diethylaminopropiophenone oxime.

Normally, any of the medicaments to be microencapsuled may be used as their conventional salts, hydrates or the like.

This list is not intended to be all inclusive as any medicament which can be microencapsulated may be administered in the form of the present invention.

It has been known in the prior art to encapsulate vitamins and to add such encapsulated vitamins to foods including candies in order to fortify the foods. One would not be taught to add encapsulated, pharmaceutically active agents other than vitamins to foods from a consideration of such references because one does not fortify foods with drugs. Thus, in one aspect of the present invention the medicament may be considered to include all pharmaceutically active agents exclusive of vitamins and minerals which are conventionally used to fortify foods. However, in the preferred form of the present invention in which the microcapsules are of a size less than 300 microns, the unexpected advantage of the use of such small microcapsules would apply also to vitamins and minerals.

A broad range of encapsulating agents and methods of encapsulation may also be used in the present invention. The only limitations on the encapsulation material are that it must be such that the active core material will not come into contact with the chocolate, or other matrix, during production or storage, it must be non-toxic and harmless, it must allow the core material to become released in the stomach or gastro-intestinal tract and it must be compatible with the sweet matrix. Any capsule material known to the art may be used in the present invention and any method of microencapsulation may be used. See, for example, the methods of microencapsulation discussed in Sparks, R. E., "Microencapsulation", *Kirk-Othmer Encyclopedia of Chemical Technology*, third edition, volume 15 (1981), pages 470–493. As is well known, the microencapsulation material may be chosen for sustained release properties or for release in a preferred area of the alimentary canal (e.g., stomach or intestine). It is preferred that a method be used such that as high a weight percent as possible of the microcapsules be active material. For example, U.S. Pat. No. 4,016,254 teaches a method of microencapsulation in which the microcapsules have an average diameter of from 100μ to 300μ and which comprise 94% to 99.9% of a medicament coated by 0.1% to 6% of a coating agent. See also U.S. Pat. No. 3,119,742. Any such microencapsulation procedure known to the art or discovered by the art in the future may be used to make the encapsulated medicament for use in the present invention. The present invention does not relate to techniques of microencapsulation per se, but only to the use of microcapsules of medicaments of a specified size in a soft, sweet matrix such as chocolate.

The amount of microcapsules to be loaded into a single dosage unit will depend upon the desired dosage of the particular pharmaceutical being administered. For example, 200 mg can easily be formed into microcapsules and dispersed in a bite-size unit dosage of matrix in a manner which will be substantially undiscernible to those eating the matrix. The maximum loading of microcapsules into the matrix will to a large extent be dependent upon the size of the microcapsules, the smaller the microcapsules, the larger the amount that can be loaded without being noticed when the matrix is ingested. For very tiny microcapsules, for example on the order of the size used in carbonless copy papers, it is conceivable that amounts as high as 50%, or even more, could be used without adversely affecting the consistency of the matrix. For example, if the dosage morsel of chocolate is very small, a unit dosage of medicament in very small microcapsules may be 500 mg in 1 gram of chocolate. Such a heavy loading, however, would not be preferred as such a large amount of microcapsules would adversely affect the taste and mouth feel of the matrix and substantial breakage of the microcapsules during chewing would be possible. The loading preferably should not exceed about 25–30% of the weight of the matrix and is most preferably less than 10%, depending on the average dose of the particular medicament being administered and the desired size of the dosage unit of matrix. A substantially bite-size dosage of matrix will generally be about 1–15 g, depending on the density of the matrix. Any size which is readily taken into the mouth without first sub-dividing can be considered a "bite-size morsel".

When the matrix is chocolate, the microcapsules are preferably added to the chocolate in the process of its original production. For example, sweet chocolate and milk chocolate are made by mixing cocoa butter, sugar, chocolate liquor and, for milk chocolate, milk or milk solids. These are then refined to a fine particle size and then subjected to conching. Conching is a kneading process in which chocolate is slowly mixed, allowing moisture and volatile acids to escape while smoothing the remaining chocolate paste. Conching temperatures for sweet chocolate generally range from 55°–85° C. and from 45°–55° C. for milk chocolate. It is conventional to add flavors, emulsifiers, etc. during conching. Thus, the most appropriate time to add the microcapsules of the present invention in the chocolate production is also during conching. Of course, care must be taken that sufficient mixing occurs to obtain a substantially homogeneous distribution of microcapsules so that an accurate amount of medicament will be present in any given unit weight of chocolate.

Following conching, the product is standardized, tempered and molded in well known manners.

The microcapsules need not be added during conching, but may be added at any appropriate step during the production of chocolate, or may be added by taking completed chocolate, melting it, adding the microcapsules, mixing to homogeneity, and then again molding.

It should be understood that the manner of adding the microcapsules to the chocolate or other soft sweet matrix is not critical and any procedure can be used so long as a substantially homogeneous distribution of microcapsules is obtained. It is, of course, also important that the exact amount of medicament per unit of chocolate be known or determinable.

EXAMPLE 1

Ascorbic Acid

Preparation of Ascorbic Acid Microcapsules:

Ascorbic acid was prepared into microcapsules as follows. A first coating was prepared by adding 180 gms of hydroxypropyl methylcellulose phthalate (HP-50, Shinetsu Chemicals, Japan) to 720 ml ethanol (absolute, c.p.). To this slurry, 2,880 g methylene chloride was added slowly, while stirring. The stirring was continued at room temperature until all the solid dissolved (about 1 hour). Then, one gram pigment (Yellow Lake ZLT 3) and 18 grams talc were added. The stirring was continued for another 1 hour.

A second coating solution was then prepared by slowly adding, while stirring, 60 grams Eudragit E-100 (Rohm Pharma, Germany) to a solution of 600 ml isopropanol and 400 ml acetone. Stirring was continued until all solid was dissolved and the solution became clear. To this solution were added 300 mg pigment (Yellow Lake ALT 3) and 6 g talc, and the stirring was continued for an additional hour. Eudragit E-100 is an acrylic resin which is soluble in gastric juice to a pH of 5 and expandable and permeable above pH 5.

Ascorbic acid (vitamin C) with different mesh size was purchased and sieved with a regular dual purpose laboratory sieve shaker (Ari J. Levi Ltd.). The following samples were collected:

1. Ascorbic acid size range: 44–99$\mu$
2. Ascorbic acid size range: 150–250$\mu$
3. Ascorbic acid size range: 600–800$\mu$ The coating was performed in a modified UniGlatt fluidized bed instrument. The ascorbic acid powder to be coated was fluidized for 5–10 minutes before the coating solution was applied. The first coating applied was the HP-50 coating prepared as described above. The processing data for the equipment was as follows:

Spray velocity: 8 ml/min
Air Flap: 25–40%
Inlet temp.: 50°–52° C.
Outlet temp.: 36°–40° C.
Spray pressure: 1.5 bar At the end of the coating, the coated particles were dried by continuous fluidization for another 5 minutes. After the first layer of HP-50 was applied, the instrument was cleared and the final weight of the powder sample was adjusted to 1 kilogram. Then a second coating of Eudragit E, prepared as discribed above, was applied using the same parameters.

Dispersion of Microcapsules in Matrix:

The coated samples were sieved again and again divided into the above three size ranges. Each of the three groups were dispersed into a chocolate matrix as follows:

1700 g of bitter cooking chocolate (Elite, Ramat Gan, Israel) were heated to 55° C. in a water bath until melted. Then 51 grams of the coated material (containing 40.8 grams of ascorbic acid) were added slowly while mixing with an electrical hand mixer. The viscous mixture was mixed for an additional 5 minutes and the chocolate was poured into two plastic containers each holding 850 grams. This procedure resulted in a homogenous dispersion of the coated medicine in the chocolate matrix. The same procedure was carried out with each sample of coated ascorbic acid.

Two control chocolates were made. In the first control ascorbic acid of a crystal size of 44 to 250 microns was dispersed in the chocolate in the same manner discussed hereinabove but without first being microencapsulated. In the second control sample plain chocolate was prepared under the same procedure of melting, mixing, etc. except for the omission of the addition of any ascorbic acid whatsoever.

EXAMPLE 2

Flavor and Texture Tests

Tests were conducted to determine whether the addition of a pharmaceutical to a carrier, such as chocolate, could be detected when incorporated in encapsulated form in sizes ranging from 40 to 800$\mu$. These tests were conducted using the ascorbic acid microcapsules prepared in Example 1. The samples used were as follows:

1. plain chocolate
2. chocolate plus ascorbic acid, encapsulation size 40–99$\mu$
3. chocolate plus ascorbic acid, encapsulation size 150–250$\mu$
4. chocolate plus ascorbic acid, encapsulation size 600–800$\mu$
5. chocolate plus ascorbic acid, not encapsulated.

The slabs of chocolate were cut into approximate 5 gram samples and removed from refrigeration four hours prior to presentation to the panel members in order to bring them to room temperature.

A set of test samples consisting of one each of the above five samples was presented to each of the ten judges. Panel sessions were repeated until a total of 36 judgements on each sample had been made.

Each judge received three 5 gram samples of each experimental treatment in plastic sample cups. Each sample was assigned a randomly selected 3-digit number for presentation to the panelists. The order of sample presentation was randomized in order to minimize the order effect of sample presentation.

Panelists were instructed to taste the samples in the order indicated. Each sample was to be held in the mouth for 5 seconds, chewed slowly for 15 seconds and then swallowed. Panelists were informed to wait 10 seconds before making their judgements. Water and crackers were presented to the panelists to assist in cleansing the palate between samples, thus minimizing flavor carry-over between samples. A two minute waiting period between samples was also strictly monitored. Panelists were instructed not to go back and forth between samples.

Variations in the surface color of the chocolate samples were noted—likely a result of the remelting and hardening process. In order to mask these variations—which might wrongly influence judges' decision—all samples were presented to the judges under red lighting in a separate, controlled testing area.

The evaluations were made by checking the appropriate space on the following scale:

| Sample |
|---|
| not acidic |
| trace of acidity |
| slightly acidic |
| acidic |
| very acidic |

| Sample | |
|---|---|
| | extremely acidic |

Each judgement was quantified by assigning an integer point score corresponding to 0 if the response was "not acidic" through to 5 if the response was "extremely acidic." The 36 judgements for each sample were tabulated and the results analyzed for significant differences using the analysis of variance (ANOVA) statistical test where applicable. This test determines whether or not there is a significant difference among samples—in other words, are the differences between samples real or were they noted merely by chance. The analysis of variance conducted on panelist scores for acidity, indicated that a significant difference in acidity among samples was noted. This difference was significant at the 1% level. In other words, the probability or chance of saying there is a difference when there really is none is only 1%. Since the analysis of variance showed statistically significant results, Tukey's test was applied in order to determine which of the samples were significantly different from one another. This test completes the analysis by comparing the average scores given to the samples against each other and determining which samples are different at a given level of significance. To show the results of the Tukey's test, letters are used to indicate difference. Any two means not followed by the same letter are significantly different at the 5% level. The results are shown in the following Table I.

TABLE I

Evaluation of Acidity in Chocolate Samples - Tukey's Test

| SAMPLE | SAMPLE MEAN |
|---|---|
| Chocolate, plain | 0.25 a |
| Chocolate, 40-99μ | 0.44 a |
| Chocolate, 150-250μ | 0.55 a |
| Chocolate, 600-800μ | 3.25 b |
| Chocolate, uncoated | 4.11 c |

It can be seen that the chocolate sample containing ascorbic acid in the 40-99μ encapsulations and the sample containing 150-250μ encapsulations were not perceived as being more acidic than the plain chocolate sample. However, the chocolate sample containing an equal amount of ascorbic acid encapsulated in a size range of 600-800μ was rated as significantly more acidic than the plain chocolate, the 40-99μ encapsulated sample, and the 150-250μ containing sample. Panelists perceived no significant difference in acidity between the 150-250μ and the 40-99μ ascorbic acid containing samples. The chocolate sample containing uncoated ascorbic acid was rated as significantly more acidic than all other samples.

On the 0 to 5 point acidity scale, the chocolate sample, the 40-99μ and the 150-250μ ascorbic acid containing samples were rated, on average, as being not acidic to having a trace of acidity. The 600-800μ containing sample was rated a acidic, while the sample containing uncoated ascorbic acid was rated as very acidic. These results clearly indicate that the use of microencapsulation size as high as 600μ or more will result in significant breakage during mastication and thus release of the taste of the medicament contained in the microcapsules. Below about 250μ substantially no release of the medicament in the mouth could be detected. These results fully support applicant's claim that the use of microcapsules of a size below about 350μ provide unexpectedly superior results to the use of microcapsules above about 600μ, the latter size being that of most commercially available microencapsulated drugs at the present time.

At the same time that the panelists made an evaluation of each sample for acidity, another evaluation for grittiness was also made. This time the following scale was used:

| Sample | |
|---|---|
| | not gritty |
| | trace of grittiness |
| | slightly gritty |
| | gritty |
| | very gritty |
| | extremely gritty |

As in the acidity test, point values of 0 to 5 were given for each evaluation. The analysis of variance conducted on panelist scores for grittiness indicated that panelists noted a significant difference among samples at the 1% level of significance. The Tukey's statistical test was therefore applied in order to determine which of the samples were significantly different from one another. The results are shown in the following Table II.

| SAMPLE | SAMPLE MEAN |
|---|---|
| Chocolate, plain | 0.31 a |
| Chocolate, 40-99μ | 0.33 a |
| Chocolate, 150-250μ | 0.77 b |
| Chocolate, uncoated | 2.14 c |
| Chocolate, 600-800μ | 4.08 d |

This analysis revealed that panelists did not find a significant difference in grittiness between the plain chocolate sample and the chocolate sample containing 40-99μ size encapsulations. Panelists did, however, rate the sample containing 150-200μ encapsulations as significantly grittier than both the plain chocolate and the chocolate 40-99μ size encapsulations. The chocolate containing uncoated ascorbic acid was also found to be significantly grittier than the plain chocolate, the 40-99μ encapsulated sample and the 150-250μ encapsulated sample. The chocolate sample containing the 600-800μ size encapsulations was rated, by the panelists, as significantly grittier than all other samples.

On the 0 to 5 point scale for grittiness, panelists rated the plain chocolate sample and the chocolate containing 40-99μ size encapsulations, on average, as not gritty. The 150°-250μ encapsulated sample was most often rated as having a trace of grittiness. The sample containing uncoated ascorbic acid was most often rated by the panelists as being slightly gritty, while the sample containing 600-800μ size encapsulations was rated as very gritty. These results clearly show that microencapsulation in a size range of 150-250μ reduces the grittiness that the addition of ascorbic acid imports to the chocolate while the capsules themselves impart only a trace of grittiness to the chocolate. Micro sizes of between 40-99μ also eliminate the grittiness of the ascorbic acid while not imparting any significant grittiness to the chocolate. Larger, commercially used micron sizes were found to impart significant grittiness to the chocolate samples.

EXAMPLE 3

Theophylline

Encapsulation of Theophylline:

An acylic resin coating polymer was prepared by dissolving 170 gms Eudragit RS-100 (Rohm Pharma, Germany) dissolved in isopropyl alcohol (60%) and acetone (40%). Eudragit RS-100 is a sustained release acrylic resin preparation which is poorly permeable. The final polymer concentration was 8%. To this solution was added 0.5 gms of pigment (Blue Lake ZLT 2), 17 gms talc and 8.5 gms magnesium stearate.

One kg theophylline, crystal size between 44–800μ, was coated with the acrylic resin polymer using a modified Glatt fluidized bed coating instrument (UniGlatt). The theophylline powder was fluidized and coated with the polymer. Technical details of the coating process were:

Air Flap: 25%
Inlet air temp.: 50° C.
Outlet (product) temp.: 35° C.
Spraying air pressure: 1.5 bar
Pneumatic pressure: 6 bars
Polymer solution feeding speed: 400 ml/h
Process time: 5.5 hrs The coated powder was sieved with a regular dual-purpose laboratory sieve shaker (Ari J. Levi Ltd.) and different fractions were collected. One was in the range of 600–800μ and the other in the range of 100–150μ, the preferred range in accordance with the present invention.

The obtained microcapsules may be dispersed in a chocolate matrix in the same manner described with respect to Example 1.

Artificial Mouth Test:

A test was conducted to measure the release of theophylline from various sized microcapsules using an artificial mouth. The artificial mouth used in this test was a plastic artificial mouth model manufactured by Frasaco having upper and lower jaws with teeth of natural size and configuration.

Ten mg of coated particles prepared as described above, of each size (containing 8.3 mg theophylline), were placed on the bottom rear teeth of the model. The model was closed and pressure was applied on the top corresponding to 2 kg for 10 sec. Then a twisting of the two rows of teeth was performed for another 15 sec. The particles (or their remains) were transferred to a test tube and the teeth were washed with 2 ml of water which was collected and transferred into the tube. The test tubes were centrifuged in a clinical centrifuge for 3 min. and the supernatant was removed. The amount of theophylline in each tube was determined by u.v. spectroscopy with the following results:

I. Large crystals (600–800μ): 2.04 mg theophylline released into the medium (24.5%)

II. Small crystals (100–150μ): 24 μg theophylline were released into the medium (0.29%)

In a control experiment it was shown that the release, due to diffusion, of theophylline through 17% coating layer of Eudragit RS-100 is less than 1% during a 5 min. period. Thus, the amount of uncoated theophylline found in the large crystals sample is due to breaking of the coated crystals by the mechanical pressure and friction of the teeth. Such a substantial release using large microcapsules is unacceptable for a sustained release dosage form.

The results of this test provide further evidence of the unexpectedly superior results obtainable using the preferred microcapsule size when preparing a dosage form designed to be ingested with mastication as compared to the use of microcapsules of the commercial size, particularly when the coating is a sustained release coating.

EXAMPLE 4

Aspirin

Encapsulation of Aspirin:

Aspirin crystals (90% between 600–800μ; 10% between 300–600μ) were coated with Eudragit L (Rohm Pharma), which is an anionic copolymer based on methacrylic acid and methacrylic acid methyl ester having a ratio of free carboxyl groups to ester groups of approximately 1:1. It is resistant to gastric juice but soluble in intestinal juice from pH 6. The average calculated coating thickness was 6–6.4μ. Aspirin crystals having a size of 100–150μ were coated with Eudragit L up to the same coating thickness as for the larger crystals.

Four samples were prepared from these microcapsules. Sample A comprised the larger microcapsules embedded in chocolate at a concentration of 175 mg coated aspirin per 3.5 g chocolate (5%). Sample B comprised the larger microcapsules placed into a gelatin capsule (175 mg/capsule). Sample C comprised the smaller microcapsules embedded in chocolate as described for Sample A. Sample D comprised the smaller microcapsules placed into a gelatin capsule (175 mg/capsule).

Aspirin Release Tests:

One of these four samples were swallowed by the same person at different days, each day at the same hour and after the same meal (two hours after breakfast). Urine was collected every hour and the rate of salicylate secretion was measured and plotted against time. The results are summarized in the following Table III.

TABLE III

| Sample | Time (hours) required to get peak of salicylate secretion |
|---|---|
| A | 6–7 |
| B | 6 |
| C | 3 |
| D | 2.5 |

It is believed that the 3–4 hour time difference between the preparations with large and small microcapsules is caused by the formation of a suspension in the stomach of the small microcapsules, which are transported to the intestine in a similar way to liquids, namely as soon as it is swallowed. However, the large ("commercial size") crystals behave like solids which stay in the stomach for about 2–3 hours before leaving to the intestine.

EXAMPLE 5

Aspirin

Microcapsules of aspirin coated with hydroxyphenyl methylcellulose are prepared in microcapsules of 80–100μ in a manner similar to that described in Example 1. Each microcapsule comprised 93% aspirin and 7% coating.

A similar coating, under the same conditions, was carried out using cellulose acetylphthalate as coating material.

The above prepared microcapsules were embedded in chocolate (100 mg encapsulated material per 1.5 g chocolate) in the manner described in Example 1. When the chocolate tablet was chewed and swallowed, no unpleasant taste of the drug was detected.

EXAMPLE 6

Acetaminophen

Acetaminophen was encapsulated in 2.4% ethyl cellulose (Ethocel) and 1.0% hydroxypropyl methyl cellulose phthalate (HP-50). This coating was performed on the Aeromatic Strea-I fluidized bed apparatus. The average size of the obtained microcapsules was 80–120$\mu$. The microcapsules were embedded in chocolate (100 mg encapsulated material per 1.5 g chocolate) in the manner described in Example 1. When the chocolate tablet was chewed and swallowed, no unpleasant taste of the drug was detected.

EXAMPLES 7–13

Other Medicaments

The following drugs, each in encapsulated form with diameter of about 200–350$\mu$, are embedded in 1.5 g chocolate in the unit dosages specified. In each case no unpleasant taste or mouth feel are detected upon chewing and swallowing of the chocolate formulation.

| Example No. | Active Principle | Unit Dosage |
|---|---|---|
| 7 | Chlorpromazine hydrochloride | 200 mg |
| 8 | Chlorpheniramine maleate | 8 mg |
| 9 | Erythromycin | 250 mg |
| 10 | Ferrous sulfate heptahydrate | 167 mg |
| 11 | Nitroglycerin | 2.5 mg |
| 12 | Papaverine hydrochloride | 150 mg |
| 13 | Niacin | 250 mg |

EXAMPLE 14

Commercial microcapsules were sampled to evaluate their size. They were sieved with a regular dual-purpose laboratory sieve shaker (Ari J. Levi Ltd). The results were as follows:

| | |
|---|---|
| 1. Theotard (CTS, Israel) | 100% over 800$\mu$ |
| 2. Dexatrim (Thompson Med., N.Y.) | 95% over 800$\mu$; 5% between 600–800$\mu$ |
| 3. Theo-24 (Searle) | 100% over 800$\mu$ |
| 4. Eryc 250 mg (Parke-Davis) | 100% over 800$\mu$ |
| 5. Feosol (Menley & James) | 100% over 800$\mu$ |
| 6. Sudafed (Burroughs Wellcome) | 100% over 800$\mu$ |
| 7. Nitroglycerin (Ascot) | 100% over 800$\mu$ |
| 8. Throazine (SKF) | 100% over 800$\mu$ |
| 9. Slo-phylline (Rorer) | 100% over 800$\mu$ |
| 10. Nicobid (Armour) | 100% over 800$\mu$ |
| 11. Teldrin (SKF) | 30% over 800$\mu$; 70% between 600–800$\mu$ |
| 12. Pavabid (Marion) | 100% over 800$\mu$ |
| 13. Ornatos (Rohm Pharma, Germany) | 60% over 800$\mu$; 40% between 600–800$\mu$ |
| 14. Somophylline (Fisons) | 97% over 800$\mu$; 3% between 600–800$\mu$ |
| 15. Contac (Menley & James) | 33–40% over 800$\mu$; 60–67% between 600–800$\mu$ |

It will be obvious to those skilled in the art that various changes may be made without departing from the scope of the invention and the invention is not to be considered limited to what is described in the specification.

What is claimed is:

1. A sustained release unit dosage form for oral administration to human patients of a large dosage designed for gradual release of a pharmaceutically active principle which could cause a serious overdose if released immediately if not in sustained release form, comprising:
   a soft, sweet, palatable matrix which is sufficiently soft to allow mastication thereof without the necessity of substantial chewing, said matrix having substantially homogenously embedded therein macrocapsules of a large sustained release dosage of active principle, said microcapsules having a diameter below about 300 microns, and being present in said matrix in a quantity sufficient to provide a sustained release unit dose of said active principle in each bite-size unit of said matrix, said microcapsules being microencapsulated in gastric resistant sustained release material.

2. A dosage form in accordance with claim 1, wherein said matrix is selected from the group consisting of chocolate, fudge, marshmallow, peanut butter, carob or solid yogurt.

3. A dosage form in accordance with claim 1, wherein said matrix is one which has substantially the same consistency as chocolate.

4. A dosage form in accordance with claim 3, wherein said matrix is chocolate, carob or solid yoghurt.

5. A dosage form in accordance with claim 3, wherein said matrix is chocolate.

6. A dosage form in accordance with claim 5, wherein said matrix is sweet chocolate or milk chocolate.

7. A dosage form in accordance with claim 1, wherein said active principle is an anti-bacterial agent, analgesic, anti-histamine, decongestant, anti-inflammatory agent, anti-hypertensive agent, hypnotic, sedative, tranquilizer, alkaloid, diuretic, vasodilator, hormone or vitamin.

8. A dosage form in accordance with claim 1, wherein said microcapsules of active principle have a diameter of less than about 250 microns.

9. A dosage form in accordance with claim 1, wherein said microcapsules of active principle have a diameter of about 40–150 microns.

10. In the method of administering a unit dose of pharmaceutically active principle to a human patient in need of such active principle, comprising orally administering a unit dose of the active principle in a chewable administrative form, the improvement wherein said pharmaceutically active principle is in sustained release form in a large dosage designed for the gradual release thereof and comprises a sustained release unit dosage form in accordance with claim 1.

* * * * *